United States Patent [19]

Khonsari et al.

[11] Patent Number: 4,532,012
[45] Date of Patent: Jul. 30, 1985

[54] PRODUCTION OF HIGH PURITY PHENOL BY DISTILLATION WITH STEAM AND A SOLVENT

[75] Inventors: Ali M. Khonsari, Bloomfield; George D. Suciu, Ridgewood, both of N.J.

[73] Assignee: The Lummus Company, Bloomfield, N.J.

[21] Appl. No.: 547,077

[22] Filed: Oct. 31, 1983

[51] Int. Cl.³ .............................................. C07C 37/78
[52] U.S. Cl. ...................................... 203/53; 203/52; 203/60; 203/67; 203/69; 203/70; 203/83; 203/85; 568/754
[58] Field of Search ...................... 203/52, 53, 60, 69, 203/67, 70, 92, 93, 95–98, 39, 38, 37, 43–46, 83, 85; 568/754, 749

[56] References Cited
U.S. PATENT DOCUMENTS

| | | | |
|---|---|---|---|
| 3,335,070 | 8/1967 | Adams | 203/83 |
| 3,405,038 | 10/1968 | Kohmoto | 203/69 |
| 4,298,765 | 11/1981 | Cochran et al. | 568/754 |
| 4,351,967 | 9/1982 | Nishimura et al. | 568/754 |

Primary Examiner—Wilbur Bascomb
Attorney, Agent, or Firm—Elliot M. Olstein

[57] ABSTRACT

Phenol containing MBF impurity is distilled in the presence of water and an extraction solvent for MBF (preferably AMS and/or cumene) to recover a phenol bottoms having reduced impurities. The use of solvent permits a reduction in the amount of water used, which reduces the amount of phenol in the overhead, thereby lowering costs.

12 Claims, 1 Drawing Figure

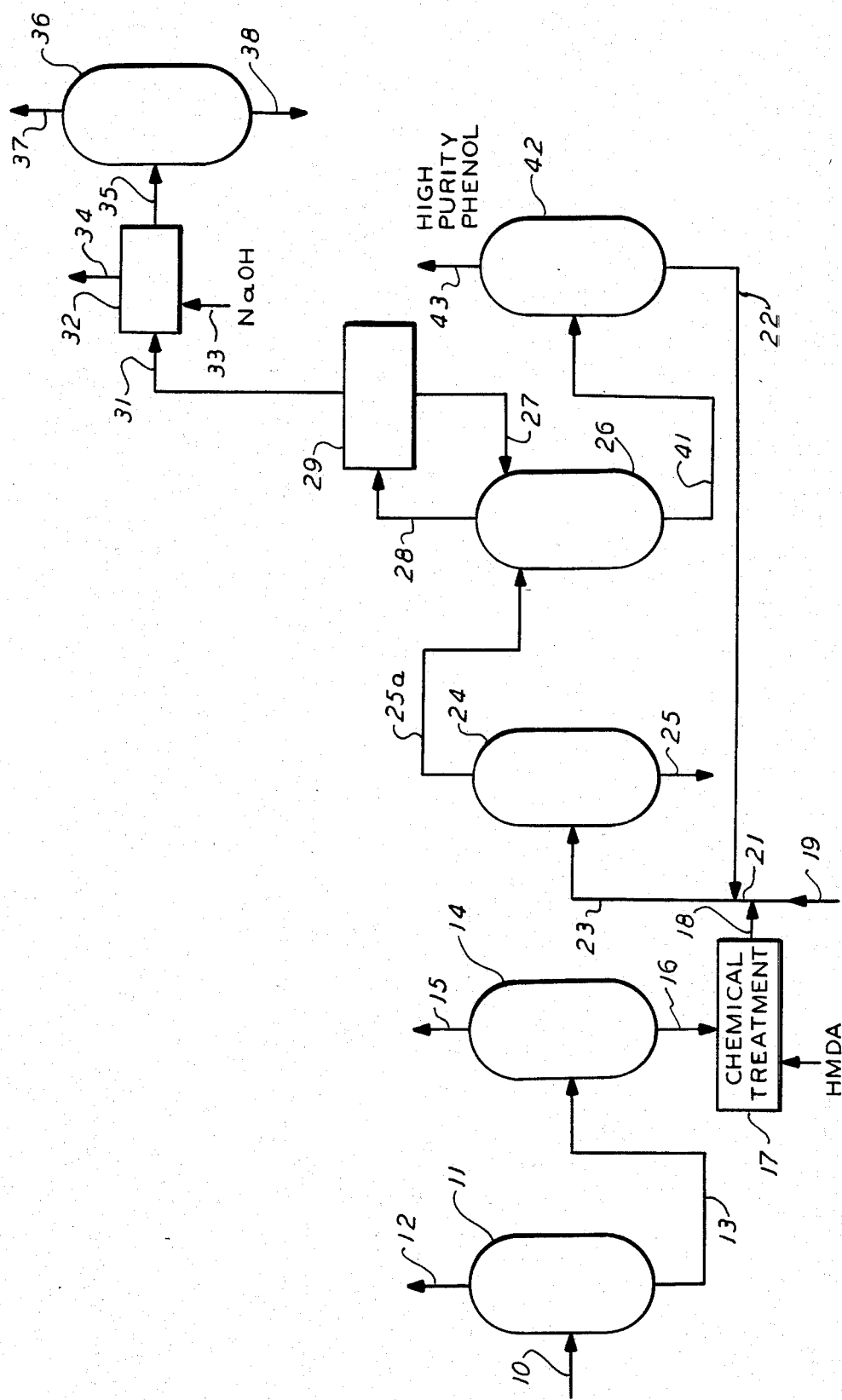

PRODUCTION OF HIGH PURITY PHENOL BY DISTILLATION WITH STEAM AND A SOLVENT

This invention relates to the production of phenol, and more particularly, to the production of high purity phenol.

Phenol may be produced from cumene by the oxidation of cumene to cumene hydroperoxide, followed by cleavage of the hydroperoxide to phenol and acetone.

In such a process, the reaction product is introduced into a separation and recovery system wherein the crude product is initially treated in a distillation column to separate acetone byproduct from the remaining mixture. The acetone-free product is then introduced into a further distillation column which operates to separate cumene from the remaining product. Optionally, the cumene recovery column can be operated to recover alpha-methylstyrene (AMS) with the cumene. If the AMS is not recovered with the cumene, the product remaining from the cumene column is introduced into a crude AMS column to separate AMS from the remaining mixture.

The product remaining from the cumene recovery column, or the crude AMS column (in the case where AMS is recovered separately from the cumene), is then introduced into a phenol recovery column to separate phenol from remaining higher boiling components.

The thus recovered crude phenol includes impurities such as acetol, mesityl oxide (MO), acetophenone, 2- and 3-methyl-benzofurans (collectively or individually methylbenzofuran or MBF), etc.

In one process, the crude phenol is chemically treated to reduce the amount of acetol and MO present in the crude phenol. Thus, for example, the crude phenol may be treated with an amine, followed by the addition of acid or acid anhydride, as disclosed, for example, in U.S. Pat. No. 3,692,485.

The resulting product is referred to as a resin or "one" grade phenol. (The phenol still contains MBF, MO and other impurities).

U.S. Pat. No. 4,298,765 describes a procedure for recovering a high purity phenol wherein, after treatment with amine, and optionally an acid or acid anhydride, the treated phenol is distilled in the presence of water to recover from the top of the column a phenol-water azeotrope which contains the majority of the MBF and other impurities initially present in the treated phenol. Water present in the azeotrope is treated to separate MBF and other impurities so as to enable recycle of such water to the distillation.

In accordance with U.S. Pat. No. 4,298,765, the water phase in the overhead is treated, after an initial separation from a phenol phase, with a solvent to extract organics therefrom, or the phenol-water mixture is treated with a solvent, non-miscible with water, followed by phase separation of organics. In such a process, a significant portion of the phenol present in the overhead is recovered in the organic phase, and it is then necessary to separately treat such organic phase to recover such significant portion of phenol. Such recovery increases overall costs.

In accordance with one aspect of the present invention, there is provided a process for purifying phenol, wherein phenol containing impurities, comprising MBF, is distilled in the presence of water and a water immiscible solvent to recover as light product, a first stream comprising phenol, essentially all of the water, extraction solvent, and most of the impurities, and as heavy product a second stream comprising phenol having a reduced quantity of the impurity. Applicant has found that, in the presence of the solvent, MBF and other impurities are removed with the light product, with a significant reduction in the amount of water fed to the column, which in turn reduces the amount of phenol present in the light product recovered from the column.

More particularly, the water is generally introduced into the distillation column in an amount somewhat in excess to that theoretically required for recovering essentially all of the extraction solvent in the light product. The use of a combination of water and solvent in the column results in a ratio of water to phenol introduced into the column which is lower than that previously employed in the art for separating MBF from phenol, which in turn, reduces the amount of phenol recovered in the lighter product. This synergistic effect of the solvent on the removal of impurities by means of distillation in the presence of water, was unexpected.

In accordance with the present invention, it is possible to separate MBF in the overhead fraction by use of a weight ratio of water to phenol which is as low as 0.05:1, preferably at least 0.1:1. In general, the water to phenol ratio does not exceed 0.8:1, and most generally does not exceed 0.5:1, as compared to prior art processes which report minimum water to phenol ratios of 1:1.

The amount (weight) of solvent required in order to perform the separation of the MBF by the present method is a multiple of the amount (weight) of the MBF present. For the range of MBF concentrations usually present in the crude phenol (30–200 ppm), the solvent is generally employed in an amount of at least 0.5%, with the solvent amount generally not exceeding 10% and most generally not exceeding 7%, all by weight, based on phenol.

The amount of solvent employed should be minimized consistent with effective removal of impurities in the light product in that an increase in the amount of solvent will necessitate an increase in the amount of water in the column, which results in a corresponding increase in the amount of phenol in the light product.

Thus, in accordance with the preferred embodiment, the solvent is employed in the amount minimally required for removal of impurities in the light product, and the water is employed in the amount minimally required for removing the solvent in the light product to thereby minimize the amount of phenol in the light product.

The phenol used as feed to the distillation column is one which has been previously distilled to separate heavies therefrom; i.e., components boiling higher than acetophenone.

The overhead fraction recovered from the distillation has a reduced amount of phenol, and such overhead is separated into an organic phase comprising the extraction solvent, impurities and some phenol, and a water phase comprising some phenol and water, which water phase may be recycled to the distillation.

In accordance with a particularly preferred embodiment, the organic extraction solvent is AMS and/or cumene, which is present in the phenol fed to the distillation, which AMS and cumene are indigenous to the process. More particularly, the phenol fed to the distillation is initially derived from the cumene recovery column which is in the separation and recovery section of the phenol production plant, and the subsequent chemical treatment of such crude phenol to reduce the content of acetol and MO is effected in a manner such that the cumene and/or AMS present in the crude phenol subjected to such chemical treatment remains in the chemically treated phenol. In accordance with prior art procedures, if cumene and/or AMS were present in the crude phenol subjected to chemical treatment, such AMS and/or cumene were removed (distilled) as lighter products during the chemical treatment. For example, the AMS and/or cumene may be retained in the chemically treated phenol by operating under reflux conditions.

In accordance with a preferred procedure, after the chemical treatment (or prior thereto), the phenol in introduced into a coarse distillation column to remove higher boilers (those present in the phenol from the cumene recovery column and/or those formed in the chemical treatment) prior to the distillation in the presence of water.

The use of a combination of water and organic solvent in the distillation column, as hereinabove noted, reduces the amount of phenol recovered in the light (overhead) product, which reduces the overall cost of the purification.

The water and organic solvent, as well as the water and phenol, are recovered as azeotropes in the overhead product, along with the impurities. Applicant has found that a heavy product (bottoms) of phenol can be recovered which is essentially free of organic solvent and water and which contains MBF in an amount no greater than 10–25 ppm, as compared to an MBF content in the feed in the order of 50–200 ppm.

It is to be understood that it is not necessary to remove all of the extraction solvent as overhead (some extraction solvent can be recovered in the phenol bottoms) in that the solvent may be subsequently separated from the phenol. It is preferred, however, to minimize (and most preferably eliminate) the solvent from the phenol bottoms.

The extraction solvent used in the distillation may be any one of a wide variety of organic solvents which are not miscible with water, and which are capable of extracting MBF and other impurities from a phenol-water mixture. In general, aromatic hydrocarbons are preferred. As representative examples of suitable solvents, there may be mentioned: aliphatic hydrocarbons (hexane, heptane, etc.), aromatic hydrocarbons (benzene and alkyl benzenes, and alkenylbenzenes), chlorinated hydrocarbon (chloroform, carbon tetrachloride, etc.) esters (ethylacetate, etc.), and others. Mixtures of solvents can also be used. Preferred are solvents which have a good extraction capacity for MBF and other impurities and which have a low solubility in water. As hereinabove indicated, cumene and/or AMS are preferred in that such solvents are indigenous to the process and therefore no additional purity problems are generated by their presence.

The overhead product from the distillation column is condensed, and the condensed product is separated into an organic and an aqueous phase. The separated aqueous phase may be recycled to the distillation. Appropriate amounts of makeup water are added to the recycle in order to compensate for the water which may have dissolved in the organic phase. The makeup water need not be pure. Any aqueous stream from the phenol plant can be used if it is similar in composition with the recycled stream.

Although recycling of the entire water phase to the distillation is preferred, it is to be understood that all or a portion of the water phase may not be recycled to the column, but treated in a known manner for recovering phenol values therefrom (for example, by distillation, etc.).

The separated organic phase, which contains the organic extraction solvent, MBF and other impurities, and some phenol, after separation from the aqueous phase, may then be treated in any of the known ways, such as with a base (for example, sodium hydroxide) to recover any phenol present therein in an aqueous phase in which the phenol dissolves as a phenate. Such water soluble phenate may be subjected to a "springing" operation, as known in the art, in order to recover the phenol.

The remaining organic may then be treated to recover extraction solvent for recycle to the distillation. In the case where the extraction solvent is cumene, which is indigenous to the process, such cumene may be recovereed for recycle to the phenol production; for example, the cumene may be separated from heavier components, including MBF, by a distillation operation.

The distillation of crude phenol, in the presence of water and the organic extraction solvent to separate impurities comprising MBF, is generally accomplished in a distillation column, which when operated at approximately atmospheric pressure, will have an overhead temperature of from 98° to 99° C., and a bottoms temperature from 182° C. to 185° C. The operating pressure can be atmospheric, or either higher or lower than atmospheric pressure, without departing from the teachings of the invention (the overhead temperature is the boiling temperature of the azeotrope at the prevailing pressure). It should be understood that the overhead and bottoms temperatures will vary with the pressure employed, moisture and amount of solvents used.

The composition of the product recovered at the top of the tower corresponds, or is close to that of mixtures of the azeotropes formed from the phenol, solvent and water at the operating pressure.

The phenol recovered as a bottoms product from the distillation procedure, in the presence of water, includes heavier components, and such phenol bottoms product may then be further treated to separate phenol from the heavier components; for example, the phenol bottoms may then be treated by a further distillation to separate high purity phenol from such heavier components.

The crude phenol feed employed in the distillation in the presence of water and solvent, as hereinabove noted, is one which has been chemically treated in order to reduce the content of acetol and MO. As hereinabove noted, such treatment may be accomplished by use of a base, and in particular, an amine, and optionally an acid or acid anhydride to neutralize the amine. It should be understood, however, that the present invention is not limited to such a feed.

The invention will be further described with reference to the drawing, wherein: the drawing is a simitified schematic flow diagram of an embodiment which incorporates the present invention.

It is to be understood, however, that the scope of the invention is not limited to the preferred embodiment.

Referring now to the drawing, a reaction effluent recovered from the reaction section of a procedure for producing phenol by the oxidation of cumene to cumene hydroperoxide, followed by acid cleavage of the hydroperoxide to phenol and aceton, in line 10, includes, as principal components, phenol, acetone, cumene, alphamethylstyrene, and as primary impurities, MBF, acetophenone, acetol, MO, etc., is introduced into an acetone recovery column, schematically designated as 11, which is operated so as to recover acetone as an overhead through line 12, and a remaining bottoms product through line 13.

The bottoms product in line 13 is introduced into a cumene recovery column, generally designated as 14, operated at conditions to recover cumene and AMS as overhead through line 15. The cumene recovery column 14 is specifically operated in a manner such that there is AMS present in the bottoms product recovered through line 16 for use, as hereinafter described, in the procedure of the present invention directed to separation of MBF from phenol. In general, some cumene is also present in the bottoms in line 16.

The bottoms in line 16 includes phenol, as well as cumene and AMS, and as impurities, MO, MBF, acetol and acetophenone, etc.

The bottoms in line 16 is then introduced into a chemical treatment zone, schematically generally indicated as 17, wherein the bottoms is treated with an amine to reduce the quantity of acetol and MO in the crude phenol. The amine is preferably hexamethylenediamine. The chemical treatment is effected in a manner such that acetol and MO are converted to higher boiling components. In accordance with the present process, chemical treatment is accomplished in a manner such that the cumene and AMS remain in the liquid phase, as compared to the prior art procedure wherein cumene and AMS concentrate in the vapor phase and are removed from the crude phenol product.

The chemically treated phenol from chemical treatment zone 17, in line 18, is then optionally treated with acid provided through line 19 (in particular phthalic anhydride), so as to neutralize the excess base used in the chemical treatment. The acid treated stream in line 21 is combined with heavier components, in line 22, obtained as hereinafter described, and the combined stream in line 23 is introduced into a column, schematically generally indicated as 24, in which a coarse distillation operation is performed, in order to separate higher boiling components, from the crude phenol stream introduced through line 23. As hereinabove indicated, the acid addition may be eliminated without adversely affecting the process.

The heavier components recovered from column 24 through line 25 may then be further treated by procedures known in the art, in order to recover more of the phenol contained therein.

The overhead stream recovered from column 24 through line 25a includes phenol, as well as cumene and AMS, which will function as the organic solvent in the subsequent distillation, and as impurities, MBF, small amounts of MO, some aceton and other impurities. The crude phenol in line 25a is essentially free of materials which boil higher than acetophenone. The crude phenol in line 25 is introduced into the upper portion of an azeotropic distillation column, schematically generally indicated as 26, along with an aqueous phase, in line 27, obtained as hereinafter described.

The column 24 is provided with a suitable known means for effecting heating thereof, such as a side boiler (not shown). Alternatively, live steam may be introduced into the azeotropic column 26.

The column is operated at a temperature and pressure to separate impurities from phenol, e.g., the conditions hereinabove described. Azeotropes, which include water, phenol, the cumene-AMS solvent and impurities, such as MBF and the like, are recovered from the top of the column through line 28.

The overhead in line 28 is cooled (not shown) in order to effect condensation thereof. The condensed overhead is introduced into a separation zone, schematically generally indicated as 29 to separate the condensed overhead into an aqueous phase and an organic phase.

The aqueous phase, which is comprised of phenol and water, and which contains a reduced amount of impurities, is recycled to the column 26 through line 27.

The separated organic phase, comprised of the AMS and cumene, which function as an extraction solvent, as well as most of the phenol contained in the azeotropes, and impurities, including MBF, is withdrawn from the separation zone 29 through line 31, and introduced into zone 32, wherein the organic phase is contacted with aqueous base, such as sodium hydroxide, introduced through line 33 for the purpose of converting any phenol to sodium phenate, which is water soluble, while MBF and other impurities are not, whereby they remain in the organic solvent. Such recovery of phenol from an organic phase is well known in the art, and no further details are required for a complete understanding of the present invention.

Aqueous sodium phenate is recovered from zone 32 through line 34 for subsequent treatment to recover phenol.

The organic phase, which is now essentially free of phenol, is withdrawn from zone 32 through line 35 for further treatment, as required, in order to recover cumene therefrom, for recycle, as feed to the phenol production. For example, as shown in the drawing, the organics in line 35 are introduced into a distillation column 36 operated to recover cumene as overhead through line 37, and AMS and heavier components, including MBF and other impurities, as a bottoms, through line 38. The bottoms in line 38 may be further treated, as desired.

The phenol, recovered from the azeotropic distillation column 26 through line 41, is introduced into a phenol recovery column, schematically generally indicated as 42 in order to separate phenol from higher boiling impurities. A high purity phenol is recovered from column 42 through line 43.

The heavier components recovered as bottoms from column 42 in line 22 are ultimately recovered from the system with the bottoms recovered from column 24.

The high purity phenol recovered from column 42 in line 43 contains less than 30 ppm of MBF, and in most cases, less than 10 ppm of MBF.

Although the invention has been described with respect to an embodiment in the accompanying drawing, it is to be understood that the scope of the invention is not limited to such an embodiment.

Thus, for example, the embodiment may be modified in numerous ways within the spirit and scope of the present invention. In one such modification, crude phenol recovered from the cumene column 14 may be intiailly treated to separate heavier components therefrom, followed by the chemical treatment to reduce the quantity of acetol and MO.

In another modification, the crude phenol may be chemically treated in the cumene recovery column.

In still another modification solvent or solvents different from AMS can be used.

As yet a further modification, the phenol feed to the chemical treatment may be a resin grade phenol (heavier and lighter components removed) and the solvent added to the azeotropic distillation column 26. The solvent could be AMS and/or cumene derived from the process, or another appropriate solvent.

As should be apparent, the present invention is not limited to a particular flow scheme, provided that the phenol feed which is distilled to separate MBF therefrom is distilled in the presence of water and an extraction solvent, as hereinabove described.

These and other modifications should be apparent to those skilled in the art from the teachings herein.

EXAMPLES 1-3

Phenol feed, including AMS and cumene, was fed continuously, by using a metering pump, to a distillation column. Prior to entering the column, the feed was mixed with a stream of water metered separately and the mixture was preheated to 90° C. The phenol had been previously treated with hexamethylene diamene and phthalic anhydride.

The water phenol mixture was fed continuously to the second tray (from the top) of a one-inch Oldershaw column having 50 actual trays. The temperature of the vapors leaving the top tray was 99° C. wile that in the reboiler was 182°-185° C.

Various flow rates of water were used while maintaining a constant feed rate for the phenol. The overhead product was condensed and the two liquid phases which formed were separated. The compositions of the feed, as well as of the bottom product and of the organic layer of the overhead product are recorded in Table 1. Phenol having the same composition was used in Examples 1, 2 and 3. The results indicate that an efficient removal of MBF and other impurities is achieved in the conditions described.

EXAMPLES 4-5

The sequence of operations of Examples 1-3 was repeated with different phenol feeds, including cumene and MAS. The phenol had been previously treated with hexamethylene diamene. The results are summarized in Table 2.

The above examples indicate that it is possible to produce high purity phenol by the procedures outlined above by making use of the finding that the presence of compounds such as cumene and AMS enhances the separation of the MBF and other impurities from phenol while the water has to be present in reasonable excess to the amounts required for removing the AMS and cumene as azeotropes from the phenol.

The overhead product contains all the water, AMS, cumene and most of the MBF and other impurities fed to the azeotropic column.

Although other compounds than AMS and cumene can be used, these are preferred since they are indigenous in the cumene technology.

TABLE 1

| | $H_2O$/Phenol Ratio | Description | Concentrations (ppm) | | | | | | |
|---|---|---|---|---|---|---|---|---|---|
| | | | Acetone | MO | Cumene | AMS | MBF | AP | DMPC |
| | | Phenol Feed | 261.8 | 40.5 | 0.986* | 1.292* | 119.1 | 1665.2 | 150.7 |
| | | Reboiler composition at start of run | 1.7 | 1.6 | 1.3 | 19.8 | 25.2 | 2076.7 | 886.0 |
| Example 1 | 0.51 | Bottom Product | 1.2 | 0.3 | — | 11.3 | 18.0 | 2047.8 | 563.1 |
| | | OVHD, Org. Phase | 2340.3 | 807.2 | 15.15* | 23.08* | 1983.2 | 4293.7 | 509.2 |
| Example 2 | 0.22 | Bottom Product | 0.9 | 1.3 | — | 9.1 | 13.8 | 1935.4 | 376.2 |
| | | OVHD, Org. Phase | 3463.8 | 981.8 | 23.26* | 31.91* | 2653.1 | 3575.5 | 279.5 |
| Example 3 | 0.13 | Bottom Product | 1.6 | 2.9 | 0.8 | 13.0 | 11.1 | 1744.7 | 302.3 |
| | | OVHD, Org. Phase | 4355.0 | 1051.0 | 27.09* | 37.16* | 3141.4 | 3158.5 | 281.2 |
| | | OVHD, Aqueous Phase | 629.9 | 1.6 | 14.7 | 37.4 | — | 7.4 | — |

NOTES:
*Concentration in wt. %
MO—Mesityl oxide
AMS—Alpha methyl styrene
MBF—Methyl benzofurans
AB—Acetophenone
DMPC—Dimethyl-phenyl-carbinol

TABLE 2

| | $H_2O$/Phenol Ratio | Description | Concentrations (ppm) | | | | | | |
|---|---|---|---|---|---|---|---|---|---|
| | | | Acetone | MO | Cumene | AMS | MBF | AP | DMPC |
| Example 4 | 0.11 | Feed | 208.8 | 31.4 | 531.0 | 3.130* | 119.2 | 2544.5 | 103.9 |
| | | Bottom Product | 0.8 | 4.0 | 5.4 | 29.7 | 12.5 | 2954.9 | 62.9 |
| | | OVHD, Org. Phase | 2956.5 | 628.5 | 1.178* | 64.210* | 2654.4 | 3429.0 | 643.8 |
| Example 5 | 0.085 | Feed | 232.3 | 14.1 | 0.913* | 1.510* | 121.1 | 1930.3 | 276.5 |
| | | Bottom Product | 1.6 | 1.9 | 2.9 | 27.7 | 16.8 | 2012.0 | 75.4 |
| | | OVHD, Org. Phase | 3806.7 | 332.0 | 24.40* | 42.02 | 3246.0 | 2884.1 | 296.0 |

*Concentrations in wt. %

EXAMPLES 6-7

In comparative runs, the phenol feed contained essentially no AMS and cumene.

Chemically treated phenol (hexamethylenediamine followed by phthalic anhydride) was used as feed in the steam distillation which was carried out as described in Example 1. The phenol depleted of MBF was removed continuously from the reboiler while the azeotropic overhead was removed using a condenser above the 52nd tray. The results obtained are given in Table 3.

These examples show that in absence of the solvents (AMS and cumene), the amount of water needed for reducing the concentration of MBF to a predetermined value is much higher than in the presence of the solvents, as in the present invention.

TABLE 3

| | Sample Description | Total Impurities (ppm) | MBF (ppm) | Water/Phenol Weight Ratio |
|---|---|---|---|---|
| Example 6 | Feed | 674 | 102 | 0.52 |
| | Bottom Product | 117 | 12 | |
| | Overhead (Organic Phase) | 17028 | 4108 | |
| | Overhead (Aqueous Phase) | 170 | 23 | |
| Example 7 | Feed | 775 | 101 | 0.28 |
| | Bottom Product | 173 | 45 | |
| | Overhead (Organic Phase) | 18108 | 3892 | |
| | Overhead (Aqueous Phase) | 253 | 20 | |

The present invention is particularly advantageous in that it permits recovery of a high purity phenol, without the necessity of simultaneously producing a resin grade phenol.

The high purity phenol is produced by removal of MBF and other impurities in an azeotropic distillation column, while minimizing the amount of phenol in the overhead from such column (which reduces overall process cost). These and other advantages should be apparent to those skilled in the art from the teachings herein.

Numerous modifications and variations of the present invention are possible in light of the above teachings and, therefore, within the scope of the appended claims, the invention may be practiced otherwise than as particularly described.

What is claimed is:

1. A process for producing high purity phenol, comprising: introducing phenol containing methylbenzofurans as an impurity, water, and a water immiscible organic extraction solvent for methylbenzofurans into a steam distillation zone, said water being introduced in an amount to provide a water to phenol ratio of at least 0.05 to 1 and no greater than 0.8 to 1 and said extraction solvent being introduced in an amount to provide extraction solvent in an amount of at least 0.5% and no greater than 10% all by weight of the phenol introduced into the steam distillation zone to reduce the quantity of phenol recovered as light product; and distilling the phenol in the steam distillation zone in the presence of the water and extraction solvent to recover a light product comprising phenol, water, extraction solvent and impurities, and a heavy product comprising phenol having a reduced quantity of impurities.

2. The process of claim 1 wherein the water to phenol ratio is no greater than 0.5:1.

3. The process of claim 2 wherein the extraction solvent does not exceed 7% of the phenol introduced into the distillation zone.

4. The process of claim 1 wherein the organic extraction solvent is comprised of at least one member selected from the group consisting of cumene and alpha-methylstyrene (AMS), said member being present in the phenol feed to the distillation zone.

5. The process of claim 1 and further comprising: separating the light product into an aqueous phase comprising phenol and water, and an organic phase comprising extraction solvent, said impurities and some phenol, and recycling aqueous phase to said distillation zone.

6. The process of claim 4 wherein the water to phenol ratio is no greater than 0.5:1.

7. The process of claim 6 wherein the extraction solvent does not exceed 7% of the phenol introduced into the distillation zone.

8. The process of claim 7 wherein the heavy product contains no greater than 10 to 25 ppm of methylbenzofurans (MBF).

9. The process of claim 7 wherein the light product is recovered as an azeotropic overhead from the distillation zone.

10. A process for purifying a crude phenol containing methylbenzofurans as an impurity, comprising: introducing water, a water immiscible organic extraction solvent for methylbenzofurans and phenol containing methylbenzofurans as an impurity into a steam distillation zone, said phenol being essentially free of materials which are higher boiling than acetophenone, said water being introduced to provide steam for said steam distillation, said water being introduced in an amount to provide a water to phenol ratio of at least 0.05 to 1 and no greater than 0.8 to 1 and said extraction being introduced in an amount of at least 0.5% and no greater than 10% to provide a phenol bottom product containing no greater than 10 to 25 ppm of methylbenzofurans which is essentially free of extraction solvent, said steam distillation column being operated at an overhead temperature corresponding to the azeotropic boiling temperature of overhead product; recovering phenol as a bottoms product from the steam distillation column, said phenol bottoms product being essentially free of water and extraction solvent and containing no greater than 10 to 25 ppm of methylbenzofurans; and recovering an overhead product from the steam distillation zone comprising extraction solvent, water, some phenol and methylbenzofurans.

11. The process of claim 10 wherein the water to phenol ratio is no greater than 0.5:1.

12. The process of claim 11 wherein the organic extraction solvent is comprised of at least one member selected from the group consisting of cumene and AMS, said member being present in the phenol feed to the distillation zone.

* * * * *